United States Patent [19]

Buysch et al.

[11] Patent Number: 5,583,251

[45] Date of Patent: Dec. 10, 1996

[54] PROCESS FOR THE PRODUCTION OF ISOCYANATES AND FOR THE PRODUCTION OF LIGHT-COLORED FOAMS THEREFROM

[75] Inventors: Hans-Josef Buysch; Manfred Gallus; Herbert Gebauer; Otto Immel, all of Krefeld; Christine Mendoza-Frohn, Erkrath; Reinhard Langer, Krefeld, all of Germany

[73] Assignee: Bayer Aktiengesellschaft, Leverkusen, Germany

[21] Appl. No.: 414,543

[22] Filed: Mar. 31, 1995

[30] Foreign Application Priority Data

Apr. 7, 1994 [DE] Germany .............. 44 11 911.9

[51] Int. Cl.$^6$ .............................................. C07C 263/10
[52] U.S. Cl. .............................................. 560/347
[58] Field of Search .............................................. 560/347

[56] References Cited

U.S. PATENT DOCUMENTS

| | | | |
|---|---|---|---|
| 3,932,514 | 1/1976 | Thelen et al. | 260/586 P |
| 4,265,834 | 5/1981 | Birkenstock et al. | 564/421 |
| 4,407,733 | 10/1983 | Birkenstock et al. | 502/174 |
| 4,465,639 | 8/1984 | Hatfield, Jr. | 260/453 PH |
| 4,774,357 | 9/1988 | Keggenhoff et al. | 560/352 |
| 4,876,380 | 10/1989 | Chen et al. | 560/352 |
| 5,426,126 | 6/1995 | Gebauer et al. | 521/131 |

FOREIGN PATENT DOCUMENTS

| | | |
|---|---|---|
| 2038126 | 9/1991 | Canada . |
| 2092623 | 9/1993 | Canada . |
| 2207671 | 2/1989 | United Kingdom . |

OTHER PUBLICATIONS

Braunauer et al J. Am. Chem. Soc., vol 60 p. 309, (1938–Month unavailable).

*Primary Examiner*—Samuel Barts
*Attorney, Agent, or Firm*—Joseph C. Gil; Lyndanne M. Whalen

[57] ABSTRACT

Isocyanates or isocyanate mixtures which contain no appreciable amounts of color causing materials are produced by phosgenating the amine corresponding to the desired isocyanate and treating the isocyanate-containing phosgenation mixture with hydrogen in the presence of a supported catalyst. The supported catalyst is in a form such that its shortest dimension is from about 0.3 to about 3.0 mm. This catalyst has a BET surface of from about 0.5 to about 150 m$^2$/g. No alkali material can be present in the catalyst. These isocyanates are particularly useful for the production of light-colored foams.

4 Claims, 1 Drawing Sheet

PROCESS FOR THE PRODUCTION OF ISOCYANATES AND FOR THE PRODUCTION OF LIGHT-COLORED FOAMS THEREFROM

BACKGROUND OF THE INVENTION

The present invention relates to a process for the production of isocyanates or mixtures of isocyanates which contain no appreciable amount of color-causing materials, the isocyanates produced by this process and a process for the production of light-colored foams from these polyisocyanates.

Improved color of rigid polyurethane foams is one of the goals sought by many working in polyurethane chemistry. Pale yellow to white is the desired color. In addition to a better visual impression, light-colored foams indicate that the raw materials from which they were produced had a high degree of purity.

If a yellowish brown or grey starting material is used to produce a foam, undesirable streaks occur at the surface of the rigid foam. These streaks are due to bubbling up during the foaming process. The exact composition of the materials causing the color in polyurethane foams or of the color-causing components in the polymer has not yet been established.

The prior art teaches that the elimination of color is one of the problems addressed during the preparation of isocyanates. A number of methods for improving the color of polyurethane foams have been described in the literature.

For example, GB-A 2,207,671 discloses the use of dried magnesium silicates to remove traces of "coloring impurities" in diisocyanatodiphenylmethane (MDI) at around 190° C.

U.S. Pat. No. 4,465,639 teaches that the "dark colored material" formed during separation of the solvent in the preparation of diisocyanatodiphenylmethane, is reduced by the addition of small quantities of water.

U.S. Pat. No. 4,876,380 describes an extraction method in which polyisocyanates are separated into two fractions by using methylene dichloride and pentane. One of the fractions is a purified fraction having improved color. The color of the second fraction is not critical. Purification of polyisocyanates by extraction is also described in EP-A 0,133,538.

In EP-A 0,446,781, a method for the improvement of polyurethane foam is described. In this method, diaminodiphenylmethane (MDA) is subjected to a catalytic hydrogenation in the presence of hydrogenation catalysts and a specific water content. All of the catalysts known to be useful in catalytic hydrogenation processes are taught to be suitable hydrogenation catalysts. One of the disadvantages of this process is that during the hydrogenation, by-products which remain in the MDA are formed. Under unfavorable phosgenation conditions, these by-products still form color causing impurities in the MDI. Moreover, it is known that the formation of strongly colored compounds in amounts in the ppm range is not excluded by the phosgenation reaction.

EP-A 561,225 discloses that a distinct improvement in the color of isocyanates is achieved without adversely affecting the other important properties of the isocyanates through a simple hydrogen treatment in the presence of catalysts at 3 to 150 bar and at 100° to 180° C. However, the activity and loading capacity of the catalysts used and the improvement in color achieved are less than desirable.

SUMMARY OF THE INVENTION

It is an object of the present invention to provide a relatively simple process for the production in high yield of isocyanates or isocyanate mixtures which are substantially free of color causing substances.

It is also an object of the present invention to provide isocyanates which are substantially free of color causing impurities.

It is another object of the present invention to provide a process for the production of light colored polyurethane foams.

These and other objects which will be apparent to those skilled in the art are accomplished by phosgenating an amine to produce the corresponding isocyanate. This isocyanate is then treated with hydrogen in the presence of a supported catalyst which (1) measures at its shortest dimension from about 0.3 to about 3 mm, (2) has a BET surface of from about 0.5 to about 150 m²/g, (3) has no alkali materials present therein and carries major part of hydrogen activity material on the outer edge of the support (shell catalyst). The isocyanates produced by this process may then be reacted with an isocyanate-reactive compound in the presence of a blowing agent to produce a light colored polyurethane foam.

BRIEF DESCRIPTION OF THE DRAWING

The FIGURE illustrates one arrangement of processing equipment useful in carrying out the process of the present invention. This equipment set up was used in carrying out the reactions described in the Examples presented herein.

DETAILED DESCRIPTION OF THE PRESENT INVENTION

Figure 1:
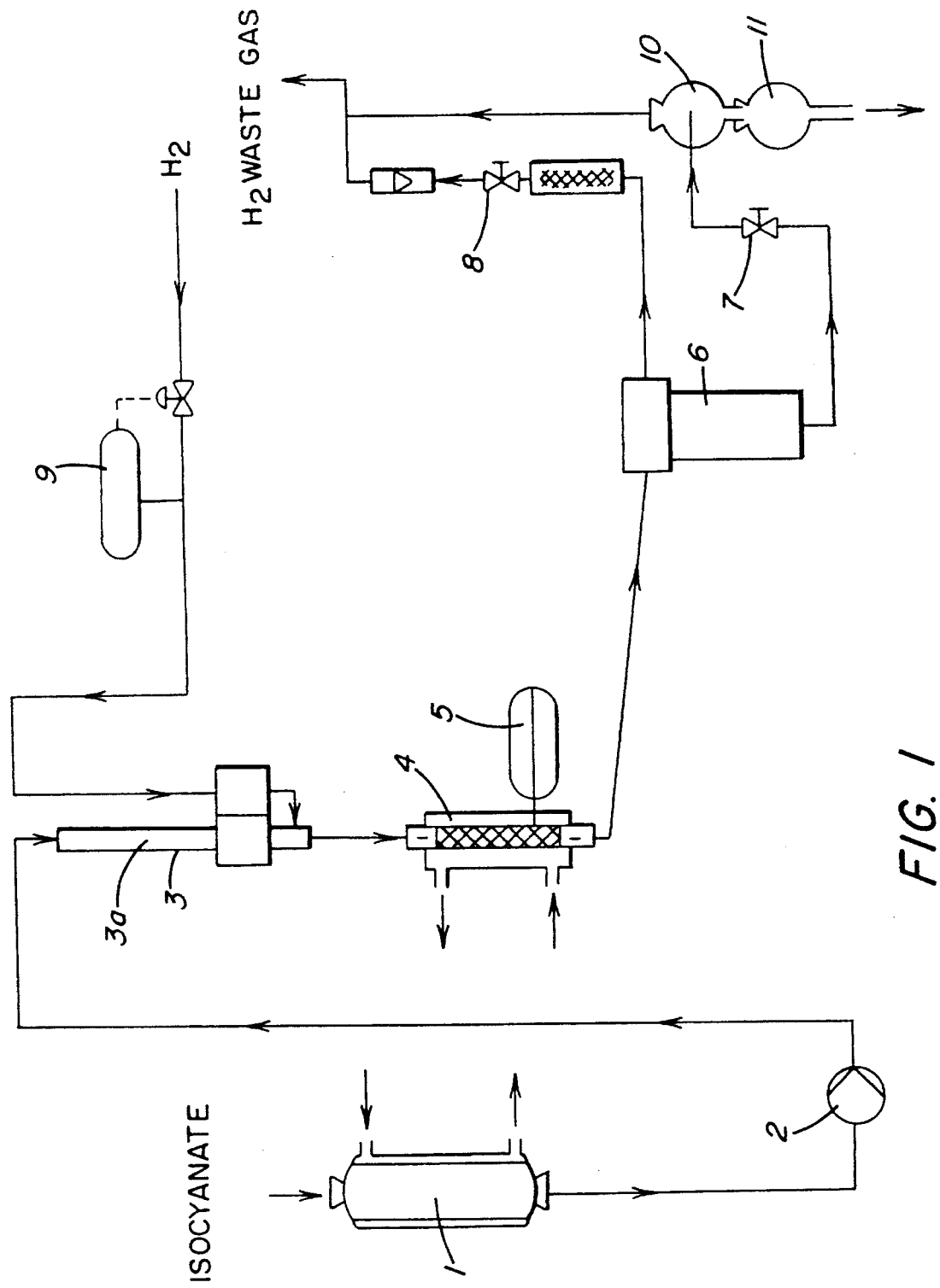

The present invention provides a process for the preparation of an isocyanate or a mixture of isocyanates which contains no color causing materials or hardly any color causing materials. In this process, the amine or amine mixture corresponding to the desired isocyanate is phosgenated. Subsequently, the isocyanate or isocyanate mixture obtained is treated with hydrogen in the presence of a supported catalyst. This supported catalyst is a shell catalyst which is from about 0.3 to about 3 mm in length along the shortest dimension, has a BET surface of from about 0.5 to about 150 m²/g and is free from alkali materials.

Surprisingly, it has been found that the process of the present invention produces isocyanates or isocyanate mixtures which have a lighter color (as compared with prior art isocyanates) at higher throughputs. The activity of the supported catalyst is also increased.

Suitable catalyst support materials include activated carbon, aluminum oxide, spinels, mixed oxides, silica, titanium dioxide and zirconium dioxide. Useful spinels and mixed oxides are, for example, represented by the formulae

and

in which
    $Me^{I}$ represents Li, Na, or K,
    $Me^{II}$ represents Mn, Zn, Co, Fe, Mg, Ca, or Ba and
    $Me^{III}$ represents Al, Cr or Fe.

The catalyst supports which are useful in the process of the present invention can be used in a variety of shapes. They may, for example, be spheres (with a diameter less than 3 mm), hollow extrudates in the form of rings or Raschig rings (thickness of the ring wall less than 3 mm), rods (with a diameter less than 3 mm), star-shaped extrudates (thickness of the rays less than 3 mm), wheel-shaped extrudates (thickness of the spokes and rims less than 3 mm in the shortest dimension) or irregularly-shaped broken or granular material (diameter less than 3 mm) obtained by screening with a screen having a mesh size of less than 3 mm.

The metal catalysts useful in the process of the present invention include any of those which are known to be useful in conventional hydrogenation processes. Suitable metals include platinum, palladium, ruthenium, iridium, rhodium, chromium, manganese, cobalt, nickel, silver, gold or mixtures thereof. The metal catalyst is preferably used in a quantity of from about 0.1 to about 5% by weight, based on the total weight of the support material. Platinum, palladium, ruthenium, rhodium and gold are particularly preferred catalysts. The most preferred catalyst is a mixture of platinum, ruthenium and gold.

The metal catalyst is preferably present on the outer edge of the support. For example, the metal catalyst may be in the form of hallow spheres on a spherical support (shell catalyst).

Methods for the production of shell catalysts are known. Examples of these methods are given, for example, in DE-A 2,849,002; (U.S. Pat. No. 4,265,834); DE-A 2,848,978 (U.S. Pat. No. 4,407,733); and DE-A 2,045,882 (U.S. Pat. No. 3,932,514).

The shell catalysts to be used in the practice of the present invention should be free from alkali materials. These shell catalysts should preferably be prepared without using alkali materials. If, however, the presence of alkali material is absolutely necessary during catalyst preparation, the alkali material should be removed after catalyst preparation has been completed. Removal of alkali material may be accomplished, for example, by thorough washing of the catalyst or by treatment of the catalyst with an acid. Examples of the acids which may be employed to remove alkali materials from the catalysts used in the process of the present invention include mineral acids such as HCl, $H_2SO_4$, and $H_2SO_3$; carboxylic acids such as formic acid, acetic acid, oxalic acid and carbonic acid; or carbon dioxide in water.

The BET surface (i.e., the surface determined in accordance with the method described in Brunauer, Emmett and Teller, *J. Am. Chem. Soc.*, Volume 60, page 309 (1938)) of the supported catalyst is generally from about 0.5 to about 150 $m^2/g$, preferably from about 1 to 100 $m^2/g$, most preferably from about 2 to about 80 $m^2/g$.

The process of the present invention is preferably used to produce aromatic isocyanates, particularly isocyanates of the diphenylmethane series, tolylene diisocyanate or mixtures thereof.

It is preferred that no solvent be present in the isocyanate to be treated with hydrogen in the presence of the shell catalyst. However, under certain conditions (e.g., high viscosity isocyanates), the concomitant use of solvents may be advantageous. Suitable solvents include inert hydrocarbons and chlorinated hydrocarbons such as toluene, xylene, ethylbenzene, cumene, chlorobenzene and dichlorobenzene.

The process of the present invention may be carried out on a batch basis but it is preferably carried out as a continuous process. In one of the preferred embodiments of the present invention, the isocyanate is trickled through the shell catalyst.

In another preferred embodiment, the catalyst is completely flooded with isocyanate, e.g., the supported catalyst present in the reactor is completely covered with liquid isocyanate to be treated. In this embodiment, it is preferred that the hydrogen not be charged through both the isocyanate and catalyst. Preferably, the hydrogen is charged through the liquid isocyanate under conditions similar to those present in the reactor in which the catalyst is present before the isocyanate/hydrogen mixture is conducted over the catalyst. This embodiment of the present invention may be carried out in either a descending or ascending liquid flow.

Charging the reactor with hydrogen may be carried out in a number of different ways. In one suitable method, the isocyanate is gassed with hydrogen in a vessel at a temperature close to, preferably below, that of the catalyst bed. Gassing is carried out at a pressure close to that present in the region of the catalyst bed. The liquid isocyanate which has been charged with hydrogen is then brought to the temperature of the catalyst bed. Upon heating, some of the dissolved hydrogen may return to the gaseous phase. Heating of the hydrogen-charged isocyanate is preferably carried out in such a way that gaseous hydrogen is returned by gravitational force to the vessel in which gassing takes place.

The vessel in which the isocyanate is brought into contact with the hydrogen may be an autoclave having a gassing device (for example, a stirrer to disperse the gas) or a static device to distribute the hydrogen introduced (e.g., a composite of porous sintered material or a perforated composite).

Static mixers may also be used inside tubes in which isocyanate and hydrogen are brought into contact, preferably conducted past one another in a countercurrent flow. Suitable static mixers, composites for the gassing of the liquids and stirrers for dispersing the gas are known to those skilled in the art.

It is preferable that the process of the present invention be carried out by trickling the liquid, isocyanate phase through the catalyst bed from top to bottom in a manner such that a liquid film forms around the catalyst particles and the volume between the individual particles contains hydrogen. The gas phase may be conducted through the catalyst bed from bottom to top, but is preferably conducted through the catalyst bed from top to bottom in a flow which is concurrent with that of the liquid phase.

The treatment of an isocyanate with hydrogen in the presence of a supported catalyst in accordance with the process of the present invention is preferably carried out at a temperature of from about 100° to about 180° C., more preferably from about 120° to about 170° C., at pressures of from about 20 to about 200 bar, more preferably from about 50 to about 150 bar. It is also preferred that the isocyanate be introduced at a rate of from about 0.2 to about 10 g of isocyanate/ml of catalyst per hour, more preferably from about 0.5 to about 8.0 g/ml per hour, most preferably from about 1.0 to about 6.0 g/ml per hour.

The isocyanates or isocyanate mixtures prepared by the process of the present invention may be reacted with an isocyanate-reactive material in the presence of a blowing agent to produce light-colored polyurethane foams. Suitable isocyanate-reactive compounds and blowing agents are known to those skilled in the art.

The invention is explained in more detail in the following Examples. All parts and percentages given in these Examples are parts by weight or percentages by weight, unless otherwise indicated.

EXAMPLES

The apparatus illustrated in the FIGURE was used to continuously treat an isocyanate with hydrogen in each of the Examples which follow. In each of the Examples, isocyanate was pumped from storage vessel 1 into metering device 3 via pressure pump 2. The hydrogen was reduced to the desired pressure via pressure control valve 9 of a storage tank. The isocyanate was saturated with hydrogen in the pressurized receiver 3a and then allowed to flow through reaction vessel 4 (trickling phase) which was filled with 60 ml of catalyst and heated up to 200° C. by temperature controlling device 5. The isocyanate treated with hydrogen was then separated off in separator 6 and transferred out via valve 7 to vessels 10 and 11. A small quantity of residual hydrogen was released through valve 8 as waste gas. This waste gas may optionally be used for heating purposes.

In each of the following Examples, 60 ml of catalyst were placed in reaction vessel 4. Liquid isocyanate from receiver 3a was charged with hydrogen. The isocyanate charged with hydrogen was introduced, at different rates, into reaction vessel 4 and brought into contact with the catalyst at 100 bar and 160° C.

The isocyanate used was an isocyanate of the diphenylmethane series (MDI), which is known to produce greatly discolored foams. This MDI product had the extinction values at 430 and 520 nm shown in Table 1, an NCO content of 31.4% and a viscosity of 200 mPa.s. The composition of the MDI was as follows: 46.3% 4,4'-MDI, 1.35% 2,4'-MDI, 0.01% 2,2'-MDI and approximately 52% of higher polymeric MDI components.

The assessment of the color values of the polymeric MDI and the change in color after hydrogen treatment was carried out by measuring the extinction values at 520 nm and 430 nm of a solution of 2 g of MDI in 100 ml of monochlorobenzene in a UV/VIS-spectrophotometer (Digital Photometer LP 1W which is commercially available from Lange GmbH, Berlin).

The following catalysts were used in the Examples summarized in Table 1:

Catalyst A (Comparative): 3,000 ml of α-aluminum oxide (commercially available under the designation SPH 512 from Rhone Poulenc) spheres having a diameter of 4 to 5 mm) and a BET surface of 10 $m^2/g$ was impregnated with 156 g of $H_2PtCl_6$ and 195 g of $RuCl_3$ dissolved in 1,091 ml of water, dried and reduced with hydrogen at 370° C. within 20 hours. A catalyst having 13 g Pt/l and 13 g Ru/l was obtained.

Catalyst B: The fraction of Catalyst A after coarse grinding having a grain diameter of from 1 to 2 mm.

Catalyst C (Comparative): Catalyst prepared in accordance with Example 1a of DE-B 2,849,002 using the required volume of impregnating solution to fill the pores ("incipient wetness"). α-$Al_2O_3$ (commercially available from Rhone Poulenc under the designation SPH 512) having a particle diameter of 2.4 to 4 mm and BET surface of 10 $m^2/g$ was impregnated with a 15% NaOH solution, dried, impregnated with a solution of $RuCl_3$ and $H_2PtCl_6$ in $H_2O$ (5% Ru, 5% Pt), drying, and $H_2$ reduction for 20 h at 370° C. The catalyst contained 4.8 g Pt/l and 3.7 g Ru/l.

Catalyst D: Spheres of alumina (commercially available from Condea) having a diameter of 1 mm and a BET surface of 4 $m^2/g$ were impregnated with a solution of $RuCl_3$ and $H_2PtCl_6$ ("incipient wetness") in $H_2O$ (5% Ru, 5% Pt in solution), dried, and reduced with $H_2$ at 370° C. for 20 hours. The catalyst contained 5.1 g Pt/l and 3.6 g Ru/l.

Catalyst E: Spheres of the same co-alumina used to produce Catalyst D were impregnated with a solution of $H_2PtCl_6$ and $Na_2PdCl_4$ in $H_2O$ in accordance with the procedure used to produce Catalyst A. The catalyst was dried for 10 min at 40° C. in a strong current of air, and activated by heating for 3 h at 350° C. in a current of hydrogen. The catalyst contained 13 g Pd/l and 13 g Pt/l.

Catalyst F: γ-$Al_2O_3$ (commercially available from Rhone Poulenc under the designation SPH 508) having a BET surface of 80 $m^2/g$ was crushed and screened to a size fraction of from 1 to 2 mm diameter. This fraction was then impregnated with $H_2PtCl_6$ and $RuCl_3$ in water in the same manner as was used to prepare Catalyst A. The impregnated alumina was dried for 10 min at 40° C. in a current of air, and then the catalyst was activated by heating for 20 hours at 370° C. in a current of hydrogen. The catalyst contained 13 g Pt/l and 13 g Ru/l.

Catalyst G (Comparative): The procedure used to produce Catalyst D was repeated with the exception that the alumina support was that used to produce Catalyst C and the impregnating solution was a solution in which 4% Ru and 4% Pt were present. The catalyst contained 4.5 g Pt/l and 2.5 g Ru/l.

Catalyst H (Comparative): The procedure used to produce Catalyst F was repeated with the exception that the alumina support was γ-$Al_2O_3$ (commercially available from Rhone Poulenc under the designation SPH 501) having a BET surface of 300 $m^2/g$. The catalyst contained 13 g Pt/l and 13 g Ru/l.

Catalyst J: The procedure used to produce Catalyst F was repeated with the exception that crushed γ-$Al_2O_3$ (commercially available from Rhone Poulenc under the designation SPH 512) was used. This support was impregnated with a solution of 156 g of $H_2PtCl_6$, 195 g of $RuCl_3$ and 130 g of $AuCl_4$ in 840 g of water. The catalyst contained 13 g/l respectively of Pt, Ru and Au.

TABLE 1

| Example | Catalyst | Through-put [g/ml.h] | length of test [h] | Extinction* at 430 nm | Extinction* at 520 nm | Reduction* of extinction [%] at 430 nm | Reduction* of extinction [%] at 520 nm |
| --- | --- | --- | --- | --- | --- | --- | --- |
| 1 (comp) | A | 0.3 | 166 | 0.318 | 0.048 | 9.1 | 44.2 |
| 2 | B | 0.3 | 42 | 0.194 | 0.025 | 44.6 | 70.9 |
|  |  | 1.1 | 39 | 0.186 | 0.026 | 46.9 | 69.8 |
|  |  | 2.6 | 40 | 0.212 | 0.026 | 39.4 | 69.8 |
|  |  | 3.5 | 45 | 0.230 | 0.025 | 34.3 | 70.9 |
| 3 (comp) | C | 0.3 | 65 | 0.320 | 0.073 | 13.7 | 15.1 |
| 4 | D | 0.08 | 15 | 0.213 | 0.026 | 39.1 | 69.8 |
|  |  | 1.1 | 19 | 0.240 | 0.028 | 31.4 | 67.4 |
|  |  | 2.2 | 21 | 0.238 | 0.028 | 32.0 | 67.4 |
| 5 | E | 0.6 | 25 | 0.196 | 0.020 | 44.0 | 76.7 |

TABLE 1-continued

| Example | Catalyst | Through-put [g/ml.h] | length of test [h] | Extinction* at 430 nm | Extinction* at 520 nm | Reduction* of extinction [%] at 430 nm | Reduction* of extinction [%] at 520 nm |
| --- | --- | --- | --- | --- | --- | --- | --- |
| | | 1.2 | 29 | 0.215 | 0.026 | 38.6 | 69.8 |
| | | 2.0 | 33 | 0.243 | 0.027 | 30.6 | 68.6 |
| | | 2.8 | 32 | 0.243 | 0.028 | 30.6 | 67.4 |
| | | 5.5 | 26 | 0.260 | 0.032 | 25.1 | 62.8 |
| 6 | F | 0.6 | 29 | 0.201 | 0.026 | 43.6 | 66.2 |
| | | 0.9 | 23 | 0.206 | 0.024 | 42.5 | 68.8 |
| | | 2.0 | 30 | 0.251 | 0.040 | 29.9 | 48.1 |
| 7 (comp) | G | 0.74 | 24 | 0.337 | 0.064 | 3.7 | 25.6 |
| 8 (comp) | H | 0.5 | 50 | 0.251 | 0.025 | 29.9 | 67.5 |
| | | 0.9 | 30 | 0.266 | 0.029 | 25.7 | 62.3 |
| | | 2.0 | 25 | 0.326 | 0.062 | 8.9 | 19.5 |
| 9 | I | 0.6 | 54 | 0.183 | 0.026 | 48.9 | 66.2 |
| | | 0.9 | 95 | 0.183 | 0.023 | 48.9 | 70.1 |
| | | 2.0 | 42 | 0.197 | 0.027 | 45.0 | 64.9 |
| MDI starting material (reference) | | | | 0.350 | 0.086 | | |

*(rel. to reference given in last line of Table 1)

In the comparative Example 1, only a very slight lightening of the color was achieved, even at relatively low throughput (0.5 g/ml.h). Spheres of α-Al$_2$O$_3$ having a diameter of from 4 to 5 mm and a BET surface of 10 m$^2$/g were used as the support (prior art, EP-A 561,225). Using the same catalyst as in Example 1 with the exception that the diameter of the α-Al$_2$O$_3$ spheres was reduced to from 1 to 2 mm, a considerable lightening of the color was achieved, even at a high throughputs (Example 2).

In the comparative Example 3, a catalyst which due to the conditions under which it was prepared, still contained base (NaOH or Na$_2$CO$_3$) was used. Only a slightly lighter isocyanate was obtained using this catalyst. Moreover, the experiment had to be stopped after 65 hours because of clogging in the reactor. Using a similar catalyst in which no sodium ions were present, a substantially lighter colored isocyanate was obtained (Example 4).

A catalyst having excessively large dimensions produced an isocyanate which was only slightly lighter in color (comparison Example 7) in contrast with an isocyanate produced using a catalyst made up of small spheres (Example 4).

A catalyst having an excessively large BET surface likewise produces unsatisfactory results (comparison Example 8) in contrast with catalysts having small surfaces (Examples 2, 5 and 6).

The catalyst activity can be further increased by the concomitant use of gold as a catalyst component (Example 9 in comparison with Example 6).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an isocyanate which is substantially free of color-causing materials comprising a) phosgenating an amine to produce a corresponding isocyanate, b) treating the isocyanate produced in a) with hydrogen in the presence of a shell catalyst which has 1) as its shortest dimension from about 0.3 to about 3 mm, 2) a BET surface of from about 0.5 to about 150 m$^2$/g and 3) no alkali materials present therein.

2. The process of claim 1 in which the isocyanate produced in a) is trickled through the shell catalyst from top to bottom in step b).

3. The process of claim 2 in which the hydrogen is passed through the shell catalyst from top to bottom in step b).

4. The process of claim 2 in which the hydrogen is passed through the shell catalyst from bottom to top in step b).

* * * * *